United States Patent [19]

Engström

[11] Patent Number: 5,312,731
[45] Date of Patent: May 17, 1994

[54] METHOD AND APPARATUS FOR STUDYING A REACTION PATTERN OF A CELL OR CELL AGGREGATES DURING PERFUSION WITH DIFFERENT MEDIA

[76] Inventor: Gunnar Engström, Pl 2375 Hörnea, S-910 20 Hörnefors, Sweden

[21] Appl. No.: 847,053
[22] PCT Filed: Oct. 5, 1990
[86] PCT No.: PCT/SE90/00638
  § 371 Date: Apr. 3, 1992
  § 102(e) Date: Apr. 3, 1992
[87] PCT Pub. No.: WO91/05253
  PCT Pub. Date: Apr. 18, 1991

[30] Foreign Application Priority Data
  Oct. 5, 1989 [SE] Sweden .................. 8903274

[51] Int. Cl.⁵ .............. C12Q 1/18; C12M 1/34
[52] U.S. Cl. .................. 435/32; 435/29; 435/30; 435/33; 435/34; 435/284; 435/285; 435/291; 435/298; 359/391; 359/398
[58] Field of Search .................. 435/29–40, 435/291, 284, 284, 298; 359/391, 398

[56] References Cited

U.S. PATENT DOCUMENTS

| | | | |
|---|---|---|---|
| 1,187,970 | 6/1916 | Cobb | 359/391 |
| 2,940,360 | 6/1960 | Carter, Jr. | 435/283 X |
| 2,942,520 | 6/1960 | Rose | 359/398 |
| 3,029,695 | 4/1962 | Wolf | 359/398 |
| 3,031,924 | 5/1962 | Lamal | 359/398 |
| 3,065,669 | 11/1962 | Orsi | 359/398 |
| 3,503,665 | 3/1970 | Carter | 359/398 |
| 3,620,596 | 11/1971 | Binnings | 359/398 |
| 3,726,597 | 4/1973 | Dvorak | 435/284 X |
| 3,941,567 | 3/1976 | Combaz | 359/398 X |
| 4,395,492 | 7/1983 | Rees | 435/283 |
| 4,435,508 | 3/1984 | Gabridge | 435/284 |
| 4,530,907 | 7/1985 | Peterson et al. | 435/285 X |
| 4,559,299 | 12/1985 | Rotman | 435/291 X |
| 4,647,531 | 3/1987 | Kamentsky | 435/291 X |
| 4,680,266 | 7/1987 | Tschopp et al. | 435/284 |
| 4,681,853 | 7/1987 | Hardy et al. | 435/285 |
| 4,734,372 | 3/1988 | Rotman | 435/291 |
| 4,748,124 | 5/1988 | Vogler | 435/285 X |

FOREIGN PATENT DOCUMENTS

171896 11/1991 European Pat. Off.

Primary Examiner—James C. Housel
Assistant Examiner—Milton I. Cano
Attorney, Agent, or Firm—Dvorak and Traub

[57] ABSTRACT

A method and apparatus for a high time resolution study of a reaction pattern of a cell or cell aggregates by light transmission microscopy during perfusion by different media. The apparatus comprises a light transparent chamber defining a first space for receiving a medium and a second space for receiving a cell or cell aggregates. The first space and second space are separated by a transparent slide and communicate with one another through a slit shaped opening. The slit shaped opening allows a first medium in the first space, for instance a control medium, to be drawn through the cell space by an external pump. The control medium in the first space may be replaced by a different medium, for instance a cytotoxic drug, by pumping the control medium from the first space and replacing it with the test medium. Pumping the control medium out of the first space however does not remove the control medium from the second space. The control medium is removed from the second space and replaced by the test medium when the test medium is drawn through the second space by the external pump. Accordingly, a comparison of the reaction patterns of the cell or cell aggregates may be performed to determine the effects of the control medium and test medium on cell shape, cell size, cell motility, cell death rate, and cell fluorescence among other parameters.

21 Claims, 2 Drawing Sheets

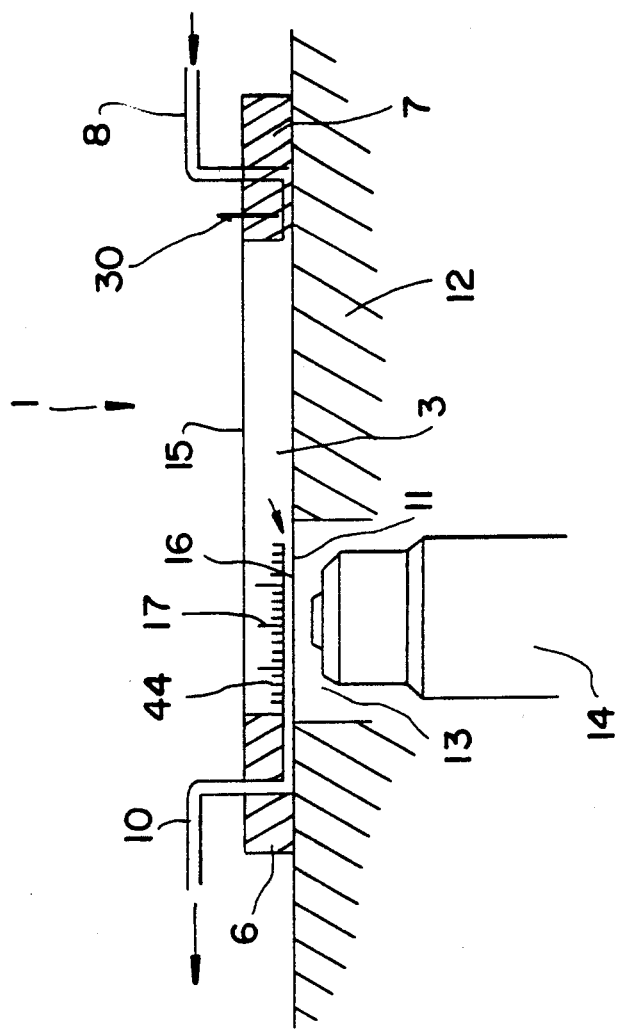

METHOD AND APPARATUS FOR STUDYING A REACTION PATTERN OF A CELL OR CELL AGGREGATES DURING PERFUSION WITH DIFFERENT MEDIA

BACKGROUND OF THE INVENTION

The present invention relates to a method and apparatus for studying a reaction pattern of a cell or cell aggregates, for instance cancer cells, by microscopy and with a high time resolution, during current perfusion (medium flowing by the cells) with at least one test medium in a liquid state, for instance containing cytotoxic drugs.

To date, cancer patients are usually treated with cytotoxic drugs according to specific programs of treatment. These programs are based on previous knowledge regarding the therapeutical spectrum of the drug or combination of drugs. The dosage and the type of drugs administered are often modified based on the rate of cancer proliferation in the patient. There may however be a considerable delay in valuable time before the dose or dosage of drugs may be modified since modification is based on the observed rate of cancer proliferation in the patient. There exists therefore a demonstrated need for an advancement in the art of determining the effect of drugs and drug dosages on a cell or cell aggregates.

It is an object of the present invention to provide a novel method and apparatus for studying a reaction pattern of a cell or cell aggregates.

It is another object of the present invention to study the response of cells or cell aggregate to different cytotoxic drugs outside the body of the patient to determine an optimum combination of cytotoxic drugs for the treatment of the patient.

It is a further object of the present invention to study the response of a cell or cell aggregates to different cytotoxic drugs over a minimal period of time.

It is a further object of the present invention to provide an apparatus for a high time resolution study of a reaction pattern of at least a cell or cell aggregates by light transmission microscopy during perfusion by different media.

The present invention is directed toward a method and apparatus of studying a reaction pattern of a cell or cell aggregates wherein the cell or cell aggregates are introduced into a small space in a perfusion chamber which is separated from a remaining, larger space in the chamber by a slide wherein the larger space functions as a reservoir for the perfusion medium. The cell or cell aggregates are then perfused with a control medium which is introduced into the larger space by a sucking means at the same time as the normal motility and reaction pattern of the cell or cell aggregates in the control medium is studied by microscopy and recorded by means of photometry, photography, and/or video recording. The sucking means is stopped and at the same time the control medium is drained from the larger space of the chamber. A test medium is then added to the larger space of the chamber. The sucking means is then restarted and the control medium in the small space is sucked out of said space, and a straight interface of test medium will simultaneously be sucked into the small space without mixing with the control medium, for reaction with the cell or cell aggregates. During the subsequent perfusion of the cell or cell aggregates it is possible to rapidly and with a high time resolution study the motility and reaction pattern of the cell or cell aggregates in the test medium by means of microscopy and record the reaction pattern by means of photometry, photography, or video. The photometry, photography, or video recordings may be studied by a computerized image processor, whereby information regarding cell shape, cell size, cell motility, cell death, cell fluorescence, etc. is obtained.

According to the present invention it is possible to determine an optimum combination of cyto-toxic drugs for treatment of the patient upon the onset of a disease. The method and apparatus of the present invention safely determine an abnormal motility and reaction pattern of the cell or cell aggregates during perfusion with a test medium, following perfusion with a control medium wherein a straight or well defined interface of test medium and control medium washes away the control medium.

These and other objects, features, and advantages of the present invention will become apparent upon consideration of the following Detailed Description of the Invention and the accompanying drawings.

BRIEF DESCRIPTION OF THE DRAWINGS

FIG. 2 is a schematic side cross-sectional view of the apparatus of FIG. 1.

FIG. 3 is a schematic side plan view of a flow damper device according to the present invention.

DETAILED DESCRIPTION OF THE INVENTION

Figure 1:
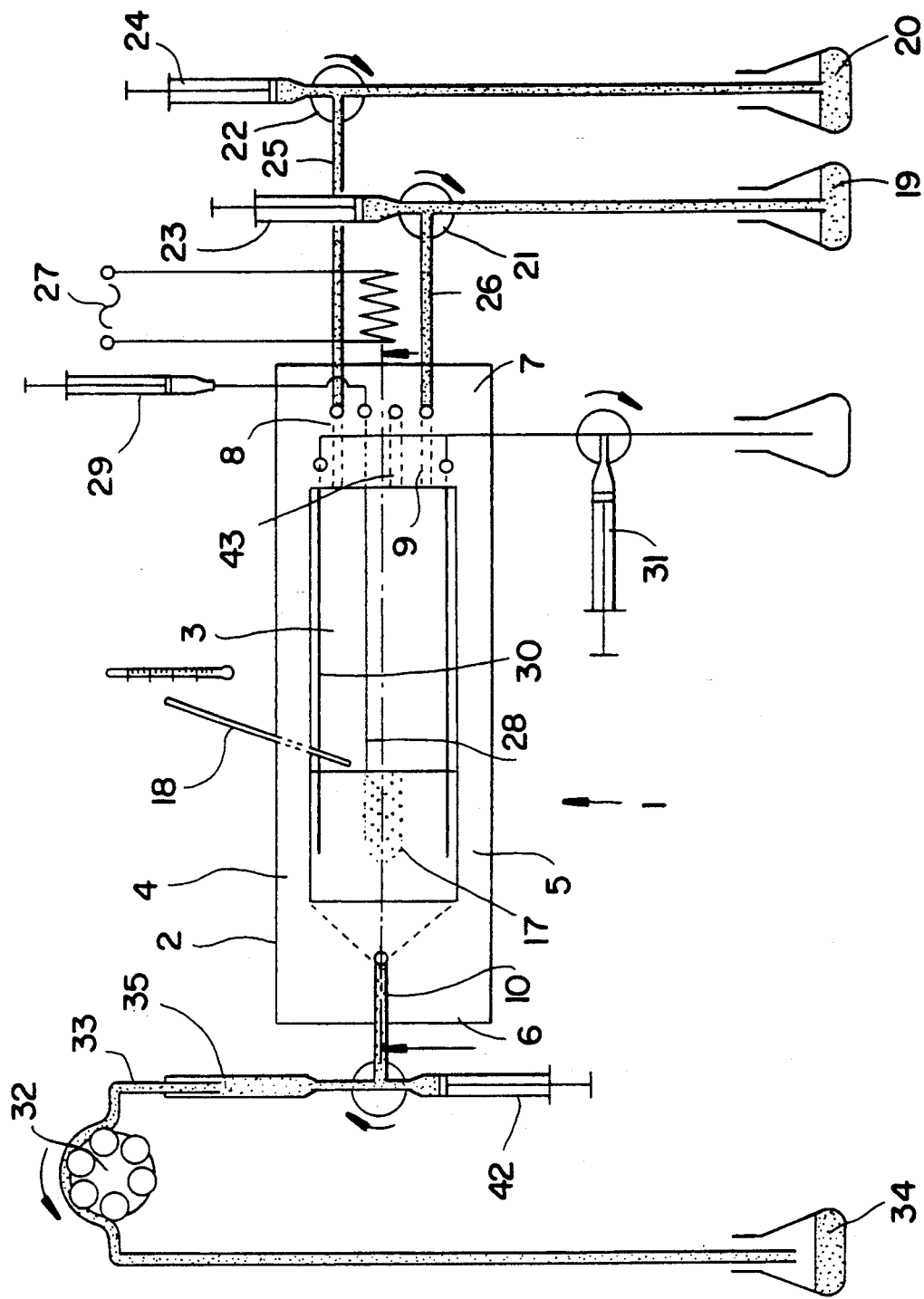
FIG. 1 is a schematic top plan view of an apparatus according to the present invention.

FIGS. 1-3 show a perfusion chamber 1 generally comprising a frame 2 essentially of rectangular shape and preferably made of a plastic material. The frame 2 is designed to include an open space 3 essentially of rectangular shape. The frame 2 comprises two long sides 4, 5 which according to one embodiment have essentially a square cross section and a width which is less than a width of two short sides 6, 7 of the frame 2 which also have essentially a square cross section. The frame 2 is essentially of standard dimensions for microscope slides, approximately 25×75 mm. According to the invention it is advantageous if the width of the frame sides 6, 7 is relatively large, to provide medium inlets to and medium outlets from the perfusion chamber 1 formed by the frame 2 via inlet channels 8, 9 and an outlet channel 10, which pass through the frame parts 6, 7 from a top surface to a bottom surface. An orifice of the inlet channels 8, 9 is located at a border portion between the bottom portion of the side 7 and the open space 3. An orifice of the outlet channel 10 is located at a border portion between the open space 3 and the bottom portion of the side 6.

The frame 2 is intended to be placed on a transparent bottom slide 11 of glass or plastic material, the latter being placed on a microscope stage 12. The chamber frame 2 is preferably glued to the bottom slide 11. The microscope stage 12 has an opening 13 in which a microscope objective 14 is intended to be positioned under the bottom slide 11 (inverted microscope) or above the perfusion chamber 1 (conventional microscope). The front part of the frame 2, with reference to the flow direction, is intended to be located above the opening 13. This means that the front half of the space 3 will be in line with the microscope objective 14. A transparent cover 15 of glass or plastic is placed on top of the frame 2 to contain a medium in the chamber 1 and prevent evaporation therefrom. The cover 15 may be made from two pieces having a circular cut-out for the objective 14 of a conventional microscope of the type that reaches down into the chamber 1.

Just above the opening of the channel 10 on the frame side 6, in the space 3, a thin transparent slide 16 is positioned, which is intended to extend backwards, in relation to the intended flow direction at a short distance from and essentially in parallel with the bottom surface plane of the frame 2. An extremely small space 17 is formed herein in which cell or cell aggregates, for example cancer cells, can be introduced. The space 17 has a volume of about 60μ according to the preferred embodiment. It is of course possible to increase the volume by increasing the distance between the bottom surface of the frame 2 and the slide 16. The larger space 3, outside the small space 17 of the chamber 1 functions as a medium reservoir, and also functions to stabilize the temperature in the chamber 1 and, in particular, in the small space 17. The medium in the chamber 1 is intended to absorb a major part of the heat generated by the microscope light. The apparatus includes a thermistor probe 18 that reads the temperature in the chamber 1. In the event of long perfusion experiments, with an insufficient chamber medium reservoir, additional medium can be supplied to the chamber 1 via the inlet channels 8, 9 connected to external reservoirs 19, 20. Thus the external reservoir 19 is connected to the chamber 1 by a valve 21 and the inlet channel 9 whereas the external reservoir 20 is connected to the chamber 1 by another valve 22 and the inlet channel 8. A syringe 23, 24 is connected to each of the two valves 21, 22 to more easily fill the system with medium and, after experimental use, to clean the chamber and tubing. The tubing 25, 26 between the reseroirs 19, 20 and the chamber 1 can be equipped with a heat-exchange means 27, as indicated in FIG. 1, by which the medium to the chamber can be cooled or heated to an appropriate temperature.

The heat-exchange means 27 may either comprise a separate heat-accumulator placed on the microscope stage 12, and through which the tubing 25, 26 is threaded, or by the microscope stage 12 as such, being in contact with the tubing 25, 26, and which functions as heating means. The tubing 25, 26 can be threaded into a tube of wider diameter for insulation.

Introduced into space 17 is a needle 28, which is connected to a syringe 29, by which means the cell or cell aggregates can be injected into the space 17.

The chamber 1, which functions as a reservoir to the medium, can be emptied by means of one or more needles and/or drain channels 30, which are inserted into/debouching into the chamber 1 and which are connected to a vacuum source such as a syringe 31.

Downstream from the chamber 1, with reference to the flow direction of the medium, is a sucking means 32. The sucking means 32 causes the medium in the chamber 1 to perfuse the cell or cell aggregates in the space 17 through the outlet channel 10, the tubing 33, the sucking means 32 and into a waste 34.

Between the sucking means 32 and the chamber 1 a flow damping means 35 can be connected to eliminate vibrations from the sucking means 32. Such vibrations may dislodge the cells in the space 17 from the bottom of the chamber 1 because the cells are attached to the glass/plastic slide 11 by simple adhesion. The cells may also be allowed to be firmly attached by growing to the bottom slide 11 of the chamber or to a separate glass slide which is introduced into the space 17 or the cells may be held by means of a micropipette, which has been introduced into the space 17.

A preferred embodiment of the flow damping means is shown in FIG. 3. The flow damper includes a cylinder-like container 36 covered by a top plug 37, and which is intended to hold both a liquid medium 38 and air 39. The air 39 functions as a damping medium. The connection between sucking means 32, via the outlet tube 40, and the liquid 38 in the container 36 is made by means of a vertically adjustable tube 41. Because the tube is adjustable it is possible to vary the air to liquid volume ratio in the container 36 and hence the damping result.

The apparatus may also include a syringe with a valve 42, placed between the flow damper 35 and the chamber 1. Hereby, the space 17 and the reservoir 3 can be flushed by a medium which is taken out by the syringe 42.

As previously described, the chamber 1 is equipped with a top cover 15. By simply removing the top cover 15 good access is provided to the slit-shaped opening between the cell space 17 and the remaining space 3 in the chamber 1. Thus, cells can be easily added and washed away between the experiments. Furthermore, micropipettes can be introduced into the cell space 17 for the manipulation of cells during current perfusion. This option opens another application for the new invention.

The apparatus can also include an air channel 43, which goes through the frame part 7, and is intended to connect the space 3 of the chamber 1 to the atmosphere. The air channel 43 makes it possible for the cover slide 15 to remain in position during the experimentation, which can be of advantage when using dangerous cytotoxic drugs harmful to personnel.

The apparatus of the invention is used as follows: Cells, for example cancer cells, are introduced into the space 17, followed by a perfusion for an appropriate period of time, for instance 15 minutes, by means of a control medium which has been added to the chamber 1, for instance, from the first reservoir 19. The motility and reaction pattern of the cell or cell aggregates is studied during the control perfusion. The cells are simultaneously recorded by photometry, photography, and/or video to be analyzed by a computerized image processor whereby cell shape, cell size, cell motility, cell fluorescence, and/or cell changes of other kinds can be efficiently studied. The control medium is then drained from chamber 1 by the syringe 31, after which time the connection between the chamber 1 and the second reservoir 20 is opened, the latter holding a test medium for instance containing cyto-toxic drugs in a liquid state. The chamber 1 is then filled with the test medium. The medium surrounding the cells in the space 17 will not be affected during the draining of the first medium from the chamber 1 because the sucking means 32 is not operating during the medium exchange. The time needed for the medium exchange procedure as such is usually 5 to 10 seconds.

When the sucking means 32 is restarted, a distinct medium exchange will take place in the cell space 17 because of its small volume and because a close to straight or well defined interface of test medium moves towards the cells and pushes the control medium, remaining in the space 17, ahead. Thus the cells will be perfused again, but this time with the test medium that contains the cyto-toxic drug. Simultaneous changes to the cancer cells due to the exposure to the cyto-toxic drug can then be studied by means of microscopy and recorded by photometry, photography, and/or video. A high time resolution is hereby provided (seconds for the study of acute, rapid changes to cells in response to test a medium or compounds.

It is of course possible to modify the apparatus. For instance, the chamber frame 2 could be made of stainless steel instead of plastic. Furthermore, the chamber could be in one piece instead of letting the frame 2 be attached to a bottom slide 11, and a top cover 15. The frame 2 can also be made in two pieces with a detachable short end module which is pressed in position at the place for the short side 7 and which is equipped with the holes for the inlet channels 8, 9, thermistor probe 18, drain channel/drain channels 30, air channel 43 and other possible channels. This is in order to simplify the replacement of the chamber which can be made for single use and disposed after use. The frame 2 can also be provided with a mm-scale 44 along with the longitudinal axis of the frame 2, above and along both sides of the cell space 17 to determine the location of the cells under study in relation to the opening between the cell space 17 and the medium reservoir 3. This distance affects the time of cell exposure to the test medium in relation to the time when the sucking means 32 is started after the medium exchange in the reservoir 3. For use in a conventional microscope, with the objective 14 coming from above instead of from below, according to FIG. 2, the chamber 1 can also be designed for use upside-down on the microscope stage 12. In this connection it is needed to modify the channels 8, 9, 10, and 43, to be accessible in the frame 2, and the slide 15 must be attached to the frame 2 whereas the slide 11 is made detachable instead. The enclosed volume of the chamber 1 can be varied by means of a special insert, preferably made of stainless steel, to fit in the space 3. In the insert two holes are drilled to connect to the channels 8, 9, and eventually to the drain channel 30. In addition, the insert can function as a heat accumulator. The insert, including its channels, can also be designed to allow control and test media to be distributed over the entrance of the cell space 17. The apparatus, with or without insert, can also be made to allow control and test medium, respectively, to be added by an additional pump in excess to the flow that enters the cell space 17 by the sucking means 32. The excess medium escapes from the chamber 1 via the drain channel 30. By this procedure, test medium can flush towards the entrance of the cell space 17 without the need for the reservoir 3 of the chamber to be drained at medium exchange. Furthermore, the orifice of the channels 8, 9, 10, 43 and one or more drain channels 30, can be made conical to fit a conical nozzle for a corresponding tubing.

The foregoing is a description enabling one of ordinary skill in the art to make and use the preferred embodiments of the present invention. It will be appreciated by those skilled in the art that there exists variations, modifications, and other equivalents to the embodiments disclosed herein. The present invention therefore is to be limited only by the scope of the appended claims.

I claim:

1. An apparatus for a high time resolution study of a reaction pattern of at least a cell and cell aggregates by light transmission microscopy during perfusion by different media, the apparatus comprising:

an enclosed chamber having a substantially rectangular frame, a light transparent top surface, a light transparent bottom surface and a light transparent thin slide disposed essentially parallel to the light transparent bottom surface, and extending from one side of the chamber to a region in which a microscope is positioned, the light transparent thin slide defining a first space in the chamber for receiving a medium and a second space in the chamber for receiving said at least a cell and cell aggregates, the second space communicating with the first space through a slit shaped opening defined by the light transparent thin slide, wherein the chamber permits light transmission through the top surface, the first space, the light transparent thin slide, the second space, and the bottom surface of the chamber;

a microscope having a microscope objective disposed proximate the second space and proximate the light transparent bottom surface of the chamber for the study of the cell or cell aggregates disposed in the second space of the chamber;

a first external medium reservoir, the first external medium reservoir connectable to the first space of the chamber;

a second external medium reservoir, the second external medium reservoir connectable to the first space of the chamber;

a first pump coupled to the second space of the chamber, wherein the first pump draws a first medium disposed in the first space through the second space during which time a reaction pattern of the cell or cell aggregates in the presence of the first medium may be viewed by the microscope; and a second pump coupled to the first space of the chamber for removing the first medium from the first space wherein the first pump subsequently draws a second medium disposed in the first space through the second space thereby displacing the first medium from the second space while maintaining a well defined interface between the first medium and the second medium and replacing the second medium in the second space with the first medium after which time a reaction pattern of the cell or cell aggregates in the presence of the second medium may be viewed by the microscope.

2. An apparatus for a high time resolution study of a reaction pattern of at least a cell and cell aggregates by light transmission microscopy during perfusion by different media, the apparatus comprising:

an enclosed chamber having a light transparent top surface and a light transparent bottom surface, the chamber defining a first space for receiving a medium and a second space for receiving said at least a cell and cell aggregates, the second space communicating with the first space through a slit-shaped opening therebetween, defined by a light transparent thin slide, and extending from one side of the chamber to a region in which a microscope is positioned, wherein the chamber permits light transmission through the top surface, the first and second spaces, and the bottom surface of the chamber; and means for perfusing the media through the second space.

3. The apparatus of claim 2 wherein the first space is larger than the second space.

4. The apparatus of claim 3 further comprising means for viewing said at least a cell and cell aggregate in the second space by means of light transmission through the chamber.

5. The apparatus of claim 4 further comprising means for damping the perfusion of the media through the second space.

6. The apparatus of claim 2 wherein the chamber has a substantially rectangular frame.

7. The apparatus of claim 6 further comprising a light transparent thin slide disposed in the chamber essentially parallel with the light transparent bottom surface, the light transparent thin slide forming a boundary between the first space and the second space, the light transparent thin slide also forming the slit-shaped opening between the first space and the second space wherein a well defined interface is maintained between different media subsequently perfused through the second space.

8. The apparatus of claim 7 further comprising a microscope having an objective disposed proximate the second space and proximate the light transparent bottom surface of the chamber for viewing said at least a cell and cell aggregates disposed in the second space of the chamber by means of light transmission microscopy.

9. The apparatus of claim 8 further comprising:
a first medium reservoir external to the chamber;
a first inlet channel interconnecting the first medium reservoir and the chamber; and
a first valve disposed along the first inlet channel between the first medium reservoir and the chamber.

10. The apparatus of claim 9 further comprising:
a second medium reservoir external to the chamber;
a second inlet channel interconnecting the second medium reservoir and the chamber; and
a second valve disposed along the second inlet channel between the second medium reservoir and the chamber.

11. The apparatus of claim 10 further comprising a syringe coupled to the second space of the chamber by a needle.

12. The apparatus of claim 11 wherein the first medium reservoir contains a control medium and the second medium reservoir contains a test medium.

13. The apparatus of claim 12 wherein the means for perfusing is a first pump coupled to the second space by an outlet channel, the first pump also being coupled to a syringe.

14. The apparatus of claim 13 further comprising a second pump coupled to the first space by a drain channel, the second pump also coupled to a syringe.

15. The apparatus of claim 14 further comprising a flow damper having a cylindrical container containing a combination of the media and air, the cylindrical container having one end coupled to the outlet channel and a second end coupled to the first pump.

16. The apparatus of claim 15 wherein the first space of the chamber is larger than the second space of the chamber.

17. The apparatus of claim 16 further comprising a heat exchange coupled to the chamber.

18. The apparatus of claim 17 wherein the test medium is a cytotoxic drug and said at least a cell and cell aggregates are cancerous.

19. A method of studying a reaction pattern of at least a cell or cell aggregates by light transmission microscopy with high time resolution during perfusion with a media, the method comprising the steps of:
introducing said at least a cell and cell aggregates into a small space in an enclosed chamber, the chamber defining the small space and a large space wherein the small space communicates with the large space through a slit-shaped opening;
pumping a control medium disposed in the large space through the slit-shaped opening and through the small space;
studying by light transmission microscopy a reaction pattern of said at least a cell and cell aggregates during the pumping of the control medium through the small space;
replacing the control medium in the large space with a test medium;
pumping the test medium through the slit shaped opening and through the small space thereby displacing the control medium in the small space while maintaining a well defined interface between the control medium and the test medium in the second space and replacing the control medium in the second space with the test medium; and
studying by light transmission microscopy a reaction pattern of said at least a cell and cell aggregates during the pumping of the test medium through the small space after the test medium has replaced the control medium in the small space.

20. The method of claim 19 further comprising the step of recording by means of photometry, photography, or video recording the reaction patterns of said at least a cell and cell aggregates during the study of the reaction patterns by light transmission microscopy.

21. The method of claim 20 further comprising the step of studying the photometry, photography, or video recording of the reaction patterns by image processing wherein information regarding cell shape, cell size, cell motility, cell death rate, and cell fluorescence may be obtained.

* * * * *